United States Patent [19]

Thomas et al.

[11] 4,369,056
[45] Jan. 18, 1983

[54] SUBSTITUTED PYRAZOLYLMETHYL-HALOACETANILIDE COMPOUNDS AND HERBICIDAL COMPOSITIONS

[75] Inventors: Rudolf Thomas, Wuppertal; Thomas Schmidt, Haan; Jörg Stetter, Wuppertal; Ludwig Eue, Leverkusen; Robert R. Schmidt, Cologne, all of Fed. Rep. of Germany

[73] Assignee: Bayer Aktiengesellschaft, Leverkusen, Fed. Rep. of Germany

[21] Appl. No.: 153,310

[22] Filed: May 27, 1980

Related U.S. Application Data

[63] Continuation of Ser. No. 59,084, Jul. 19, 1979, abandoned.

[30] Foreign Application Priority Data

Aug. 10, 1978 [DE] Fed. Rep. of Germany ....... 2835156

[51] Int. Cl.³ .............. A01N 43/56; C07D 231/12; C07D 231/16; C07D 231/18
[52] U.S. Cl. ........................................ 71/92; 548/376; 548/377; 548/378
[58] Field of Search .................. 548/378, 377, 376; 71/92

[56] References Cited

U.S. PATENT DOCUMENTS 3,901,917  8/1975  Richter et al. .......................... 71/92
3,907,544  9/1975  Olin ........................................ 71/92
4,055,410 10/1977  Cheng ..................................... 71/92

FOREIGN PATENT DOCUMENTS 2648008 5/1978 Fed. Rep. of Germany .
2704281 8/1978 Fed. Rep. of Germany .

*Primary Examiner*—Henry R. Jiles
*Assistant Examiner*—Natalia Harkaway
*Attorney, Agent, or Firm*—Felfe & Lynch

[57] ABSTRACT

Herbicidal substituted N-pyrazolylmethyl-haloacetanilide compounds of the formula

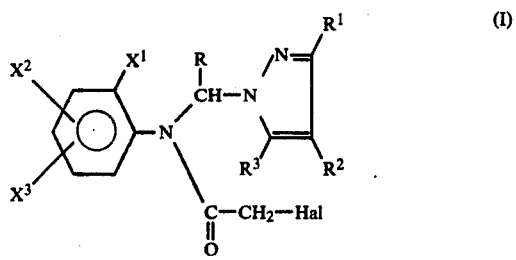

wherein
Hal is halogen;
R is alkyl, cycloalkyl, haloalkyl, alkoxyalkyl, alkenyl, alkynyl or optionally substituted phenyl;
$R^1$, $R^2$ and $R^3$ are individually selected from hydrogen, alkyl, halogen or alkoxy; and
$X^1$, $X^2$ and $X^3$ are individually selected from hydrogen or alkyl, and acid addition salts and metal salt complexes of such compounds.

31 Claims, No Drawings

SUBSTITUTED PYRAZOLYLMETHYL-HALOACETANILIDE COMPOUNDS AND HERBICIDAL COMPOSITIONS

This is a continuation of application Ser. No. 06/059,084, filed July 19, 1979, now abandoned.

The present invention relates to novel substituted N-pyrazolylmethyl-haloacetanilide compounds. In additional aspects, the invention relates to herbicidal compositions containing such compounds and methods of combating weeds utilizing such compounds.

It is known that 2,6-diethyl-N-methoxymethyl-chloroacetanilide can be used for selectively combating weeds (see R. Wegler, Chemie der Pflanzenschutz- und Schädlingsbekämpfungsmittel ("Chemistry of Plant Protection Agents and Agents for Combating Pests"), Vol. 5, page 255, Springer-Verlag (1977)). However, this compound is not always sufficiently active and its selectivity is not always completely satisfactory.

The present invention now provides, as new compounds, the substituted N-pyrazolylmethyl-haloacetanilides of the formula

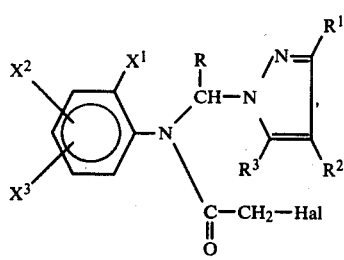

(I)

wherein

Hal is halogen;

R is alkyl, cycloalkyl, haloalkyl, alkoxyalkyl, alkenyl, alkynyl or optinally substituted phenyl;

$R^1$, $R^2$ and $R^3$, which need not be identical, each is hydrogen, alkyl, halogen or alkoxy; and $X^1$, $X^2$ and $X^3$, which need not be identical, each is hydrogen or alkyl, and their physiologically acceptable acid addition salts and metal complexes.

It has been found that the substituted N-pyrazolyl-methyl-haloacetanilides of formula (I) have powerful herbicidal properties, and, in particular, also selective herbicidal properties.

Preferably, in formula (I), Hal represents fluorine, chlorine or bromine,

R represents straight-chain or branched alkyl with 1 to 8 carbon atoms, cycloalkyl with 3 to 6 carbon atoms, haloalkyl with up to 2 carbon atoms and up to 3 identical or different halogen atoms (preferred halogen atoms being fluorine and chlorine), alkoxyalkyl with 1 to 4 carbon atoms in the alkyl part and 1 to 4 carbon atoms in the alkoxy part, alkenyl or alkynyl with in either case 2 to 4 carbon atoms or optionally substituted phenyl, preferred substituents being halogen, alkyl with 1 to 4 carbon atoms, haloalkyl with up to 2 carbon atoms and up to 3 identical or different halogen atoms (preferred halogen atoms being fluorine and chlorine), alkoxy and alkylthio with in either case up to 2 carbon atoms, cyano and nitro, $R^1$, $R^2$ and $R^3$, which may be identical or different, each represent hydrogen, straight-chain or branched alkyl with 1 to 4 carbon atoms, halogen or alkoxy with 1 to 4 carbon atoms, and $X^1$, $X^2$ and $X^3$, which may be identical or different, each represent hydrogen or straight-chain or branched alkyl with 1 to 4 carbon atoms.

The invention also provides a process for the preparation of a substituted N-pyrazolylmethyl-haloacetanilide of the formula (I), in which a haloacetanilide of the general formula

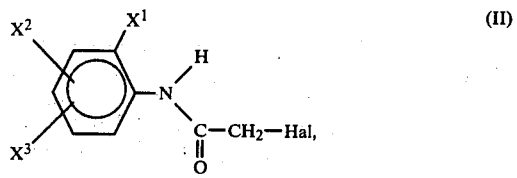

(II)

in which Hal, $X^1$, $X^2$ and $X^3$ have the meanings stated above, is reacted with a pyrazolyl derivative of the general formula

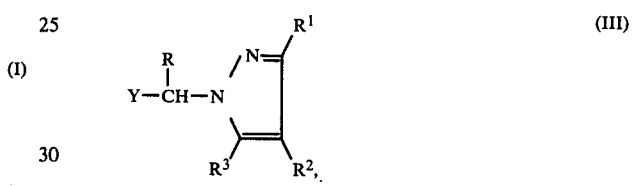

(III)

in which

R, $R^1$, $R^2$ and $R^3$ have the meanings stated above, and

Y represents halogen or the mesyl or tosyl radical, in the presence of an acid-binding agent and if appropriate in the presence of an organic solvent, and an acid or a metal salt is then optionally added on, the pyrazole derivative of the formula (III) preferably being employed in the form of a hydrogen halide salt.

Surprisingly, the substituted N-pyrazolylmethyl-haloacetanilides according to the invention have better possible uses as agents for selectively combating weeds, while having the same action against weeds, compared to 2,6-diethyl-N-methoxymethyl-chloroacetanilide, which is known. The compounds according to the invention thus represent a valuable enrichment of herbicidal agents for selectively combating weeds.

Because of the tautomeric structures in the starting substances used for their preparation, the unsymmetrically substituted N-pyrazolyl-methyl-haloacetanilides of the formula (I) exist in two isomeric forms, which can be illustrated by way of their formulae as follows:

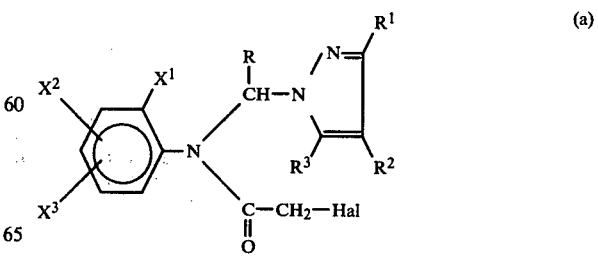

(a)

and

-continued

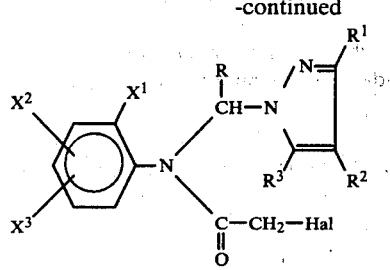
(b)

The isomer ratio is largely determined by the nature of the substituents on the pyrazole. In addition, the compounds of the formula (I) can exist as optical isomers (note the carbon atom marked by *). However, in most cases mixtures which contain all the isomers are obtained. The formula (I) includes both the position isomers and the optical isomers.

Particularly preferred compounds of the formula (I) are those in which Hal represents chlorine or bromine; R represents methyl, ethyl, n-propyl, isopropyl, isobutyl, sec.-butyl, cyclopropyl, cyclopentyl, cyclohexyl, trifluoromethyl, chloromethyl, dichloromethyl, trichloromethyl, tribromomethyl, vinyl, allyl, propen-1-yl, ethynyl, propargyl, phenyl, chlorophenyl, dichlorophenyl, methylphenyl, dimethylphenyl, chloromethylphenyl or nitrophenyl; $R^1$, $R^2$ and $R^3$, which may be identical or different, each represent hydrogen, methyl, chlorine, bromine or methoxy; and $X^1$, $X^2$ and $X^3$, which may be identical or different, each represent hydrogen, methyl, ethyl, n-propyl, isopropyl, isobutyl, sec.-butyl or tert.-butyl.

Specific examples of substituted N-pyrazolyl-methyl-haloacetanilides of the formula (I) according to the invention are:

TABLE 1

(I)

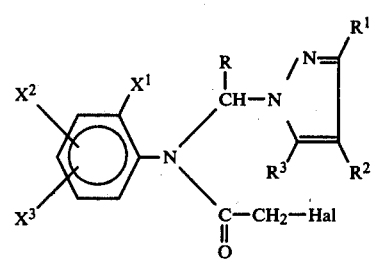

| $X^1$ | $X^2$ | $X^3$ | R | $R^1$ | $R^2$ | $R^3$ | Hal |
|---|---|---|---|---|---|---|---|
| H | H | H | CH₃ | H | H | H | Cl(Br) |
| H | H | H | CH₃ | H | Cl | H | Cl(Br) |
| H | H | H | CH₃ | CH₃ | H | CH₃ | Cl(Br) |
| H | H | H | CH₃ | CH₃ | H | H | Cl(Br) |
| H | H | H | CH₃ | H | H | CH₃ | Cl(Br) |
| H | H | H | CH₃ | CH₃ | Cl | CH₃ | Cl(Br) |
| H | H | H | CH₃ | H | OCH₃ | H | Cl(Br) |
| 2-CH₃ | H | H | CH₃ | H | H | H | Cl(Br) |
| 2-CH₃ | H | H | CH₃ | H | Cl | H | Cl(Br) |
| 2-CH₃ | H | H | CH₃ | CH₃ | H | CH₃ | Cl(Br) |
| 2-CH₃ | H | H | CH₃ | CH₃ | H | H | Cl(Br) |
| 2-CH₃ | H | H | CH₃ | H | H | CH₃ | Cl(Br) |
| 2-CH₃ | H | H | CH₃ | CH₃ | Cl | CH₃ | Cl(Br) |
| 2-CH₃ | H | H | CH₃ | H | OCH₃ | H | Cl(Br) |
| 2-C₂H₅ | H | H | CH₃ | H | H | H | Cl(Br) |
| 2-C₂H₅ | H | H | CH₃ | H | Cl | H | Cl(Br) |
| 2-C₂H₅ | H | H | CH₃ | CH₃ | H | CH₃ | Cl(Br) |
| 2-C₂H₅ | H | H | CH₃ | CH₃ | H | H | Cl(Br) |
| 2-C₂H₅ | H | H | CH₃ | H | H | CH₃ | Cl(Br) |
| 2-C₂H₅ | H | H | CH₃ | CH₃ | Cl | CH₃ | Cl(Br) |
| 2-C₂H₅ | H | H | CH₃ | H | OCH₃ | H | Cl(Br) |
| 2-i-C₃H₇ | H | H | CH₃ | H | H | H | Cl(Br) |
| 2-i-C₃H₇ | H | H | CH₃ | H | Cl | H | Cl(Br) |
| 2-i-C₃H₇ | H | H | CH₃ | CH₃ | H | CH₃ | Cl(Br) |
| 2-i-C₃H₇ | H | H | CH₃ | CH₃ | H | H | Cl(Br) |
| 2-i-C₃H₇ | H | H | CH₃ | H | H | CH₃ | Cl(Br) |
| 2-i-C₃H₇ | H | H | CH₃ | CH₃ | Cl | CH₃ | Cl(Br) |
| 2-i-C₃H₇ | H | H | CH₃ | H | OCH₃ | H | Cl(Br) |
| 2-sec.-C₄H₉ | H | H | CH₃ | H | H | H | Cl(Br) |
| 2-sec.-C₄H₉ | H | H | CH₃ | H | Cl | H | Cl(Br) |
| 2-sec.-C₄H₉ | H | H | CH₃ | CH₃ | H | CH₃ | Cl(Br) |
| 2-sec.-C₄H₉ | H | H | CH₃ | CH₃ | H | H | Cl(Br) |
| 2-sec.-C₄H₉ | H | H | CH₃ | H | H | CH₃ | Cl(Br) |
| 2-sec.-C₄H₉ | H | H | CH₃ | CH₃ | Cl | CH₃ | Cl(Br) |
| 2-sec.-C₄H₉ | H | H | CH₃ | H | OCH₃ | H | Cl(Br) |
| 2-tert.-C₄H₉ | H | H | CH₃ | H | H | H | Cl(Br) |
| 2-tert.-C₄H₉ | H | H | CH₃ | H | Cl | H | Cl(Br) |
| 2-tert.-C₄H₉ | H | H | CH₃ | CH₃ | H | CH₃ | Cl(Br) |
| 2-tert.-C₄H₉ | H | H | CH₃ | CH₃ | H | H | Cl(Br) |
| 2-tert.-C₄H₉ | H | H | CH₃ | H | H | CH₃ | Cl(Br) |
| 2-tert.-C₄H₉ | H | H | CH₃ | CH₃ | Cl | CH₃ | Cl(Br) |

TABLE 1-continued (I)

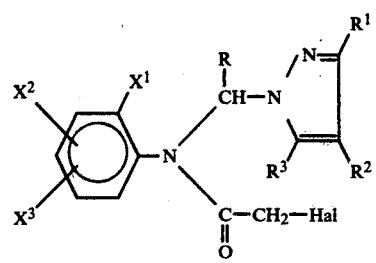

| X¹ | X² | X³ | R | R¹ | R² | R³ | Hal |
|---|---|---|---|---|---|---|---|
| 2-tert.-C₄H₉ | H | H | CH₃ | H | OCH₃ | H | Cl(Br) |
| 2-CH₃ | 6-CH₃ | H | CH₃ | H | H | H | Cl(Br) |
| 2-CH₃ | 6-CH₃ | H | CH₃ | H | Cl | H | Cl(Br) |
| 2-CH₃ | 6-CH₃ | H | CH₃ | CH₃ | H | CH₃ | Cl(Br) |
| 2-CH₃ | 6-CH₃ | H | CH₃ | CH₃ | H | H | Cl(Br) |
| 2-CH₃ | 6-C₃ | H | CH₃ | H | H | CH₃ | Cl(Br) |
| 2-CH₃ | 6-CH₃ | H | CH₃ | CH₃ | Cl | CH₃ | Cl(Br) |
| 2-CH₃ | 6-CH₃ | H | CH₃ | H | OCH₃ | H | Cl(Br) |
| 2-C₂H₅ | 6-CH₃ | H | CH₃ | H | H | H | Cl(Br) |
| 2-C₂H₅ | 6-CH₃ | H | CH₃ | H | Cl | H | Cl(Br) |
| 2-C₂H₅ | 6-CH₃ | H | CH₃ | CH₃ | H | CH₃ | Cl(Br) |
| 2-C₂H₅ | 6-CH₃ | H | CH₃ | CH₃ | H | H | Cl(Br) |
| 2-C₂H₅ | 6-CH₃ | H | CH₃ | H | H | CH₃ | Cl(Br) |
| 2-C₂H₅ | 6-CH₃ | H | CH₃ | CH₃ | Cl | CH₃ | Cl(Br) |
| 2-C₂H₅ | 6-CH₃ | H | CH₃ | H | OCH₃ | H | Cl(Br) |
| 2-C₂H₅ | 6-C₂H₅ | H | CH₃ | H | H | H | Cl(Br) |
| 2-C₂H₅ | 6-C₂H₅ | H | CH₃ | H | Cl | H | Cl(Br) |
| 2-C₂H₅ | 6-C₂H₅ | H | CH₃ | CH₃ | H | CH₃ | Cl(Br) |
| 2-C₂H₅ | 6-C₂H₅ | H | CH₃ | CH₃ | H | H | Cl(Br) |
| 2-C₂H₅ | 6-C₂H₅ | H | CH₃ | H | H | CH₃ | Cl(Br) |
| 2-C₂H₅ | 6-C₂H₅ | H | CH₃ | CH₃ | Cl | CH₃ | Cl(Br) |
| 2-C₂H₅ | 6-C₂H₅ | H | CH₃ | H | OCH₃ | H | Cl(Br) |
| 2-CH₃ | 3-CH₃ | H | CH₃ | H | H | H | Cl(Br) |
| 2-CH₃ | 3-CH₃ | H | CH₃ | H | Cl | H | Cl(Br) |
| 2-CH₃ | 3-CH₃ | H | CH₃ | CH₃ | H | CH₃ | Cl(Br) |
| 2-CH₃ | 3-CH₃ | H | CH₃ | CH₃ | H | H | Cl(Br) |
| 2-CH₃ | 3-CH₃ | H | CH₃ | H | H | CH₃ | Cl(Br) |
| 2-CH₃ | 3-CH₃ | H | CH₃ | CH₃ | Cl | CH₃ | Cl(Br) |
| 2-CH₂ | 3-CH₃ | H | CH₃ | H | OCH₃ | H | Cl(Br) |
| 2-CH₃ | 3-CH₃ | 4-CH₃ | CH₃ | H | H | H | Cl(Br) |
| 2-CH₃ | 3-CH₃ | 4-CH₃ | CH₃ | H | Cl | H | Cl(Br) |
| 2-CH₃ | 3-CH₃ | 4-CH₃ | CH₃ | CH₃ | H | CH₃ | Cl(Br) |
| 2-CH₃ | 3-CH₃ | 4-CH₃ | CH₃ | CH₃ | H | H | Cl(Br) |
| 2-CH₃ | 3-CH₃ | 4-CH₃ | CH₃ | H | H | CH₃ | Cl(Br) |
| 2-CH₃ | 3-CH₃ | 4-CH₃ | CH₃ | CH₃ | Cl | CH₃ | Cl(Br) |
| 2-CH₃ | 3-CH₃ | 4-CH₃ | CH₃ | H | OCH₃ | H | Cl(Br) |
| 2-CH₃ | 5-CH₃ | H | CH₃ | H | H | H | Cl(Br) |
| 2-CH₃ | 5-CH₃ | H | CH₃ | H | Cl | H | Cl(Br) |
| 2-CH₃ | 5-CH₃ | H | CH₃ | CH₃ | H | CH₃ | Cl(Br) |
| 2-CH₃ | 5-CH₃ | H | CH₃ | CH₃ | H | H | Cl(Br) |
| 2-CH₃ | 5-CH₃ | H | CH₃ | H | H | CH₃ | Cl(Br) |
| 2-CH₃ | 5-CH₃ | H | CH₃ | CH₃ | Cl | CH₃ | Cl(Br) |
| 2-CH₃ | 5-CH₃ | H | CH₃ | H | OCH₃ | H | Cl(Br) |
| 3-CH₃ | 5-CH₃ | H | CH₃ | H | H | H | Cl(Br) |
| 3-CH₃ | 5-CH₃ | H | CH₃ | H | Cl | H | Cl(Br) |
| 3-CH₃ | 5-CH₃ | H | CH₃ | CH₃ | H | CH₃ | Cl(Br) |
| 3-CH₃ | 5-CH₃ | H | CH₃ | CH₃ | H | H | Cl(Br) |
| 3-CH₃ | 5-CH₃ | H | CH₃ | H | H | CH₃ | Cl(Br) |
| 3-CH₃ | 5-CH₃ | H | CH₃ | CH₃ | Cl | CH₃ | Cl(Br) |
| 3-CH₃ | 5-CH₃ | H | CH₃ | H | OCH₃ | H | Cl(Br) |
| H | H | H | i-C₃H₇ | H | H | H | Cl(Br) |
| H | H | H | i-C₃H₇ | H | Cl | H | Cl(Br) |
| H | H | H | i-C₃H₇ | CH₃ | H | CH₃ | Cl(Br) |
| H | H | H | i-C₃H₇ | CH₃ | H | H | Cl(Br) |
| H | H | H | i-C₃H₇ | H | H | CH₃ | Cl(Br) |
| H | H | H | i-C₃H₇ | CH₃ | Cl | CH₃ | Cl(Br) |
| H | H | H | i-C₃H₇ | H | OCH₃ | H | Cl(Br) |
| 2-CH₃ | H | H | i-C₃H₇ | H | H | H | Cl(Br) |
| 2-CH₃ | H | H | i-C₃H₇ | H | Cl | H | Cl(Br) |
| 2-CH₃ | H | H | i-C₃H₇ | CH₃ | H | CH₃ | Cl(Br) |
| 2-CH₃ | H | H | i-C₃H₇ | CH₃ | H | H | Cl(Br) |
| 2-CH₃ | H | H | i-C₃H₇ | H | H | CH₃ | Cl(Br) |
| 2-CH₃ | H | H | i-C₃H₇ | CH₃ | Cl | CH₃ | Cl(Br) |
| 2-CH₃ | H | H | i-C₃H₇ | H | OCH₃ | H | Cl(Br) |
| 2-C₂H₅ | H | H | i-C₃H₇ | H | H | H | Cl(Br) |

TABLE 1-continued (I)

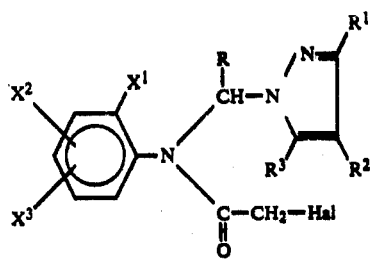

| X¹ | X² | X³ | R | R¹ | R² | R³ | Hal |
|---|---|---|---|---|---|---|---|
| 2-C₂H₅ | H | H | i-C₃H₇ | H | Cl | H | Cl(Br) |
| 2-C₂H₅ | H | H | i-C₃H₇ | CH₃ | H | CH₃ | Cl(Br) |
| 2-C₂H₅ | H | H | i-C₃H₇ | CH₃ | H | H | Cl(Br) |
| 2-C₂H₅ | H | H | i-C₃H₇ | H | H | CH₃ | Cl(Br) |
| 2-C₂H₅ | H | H | i-C₃H₇ | CH₃ | Cl | CH₃ | Cl(Br) |
| 2-C₂H₅ | H | H | i-C₃H₇ | H | OCH₃ | H | Cl(Br) |
| 2-i-C₃H₇ | H | H | i-C₃H₇ | H | H | H | Cl(Br) |
| 2-i-C₃H₇ | H | H | i-C₃H₇ | H | Cl | H | Cl(Br) |
| 2-i-C₃H₇ | H | H | i-C₃H₇ | CH₃ | H | CH₃ | Cl(Br) |
| 2-i-C₃H₇ | H | H | i-C₃H₇ | CH₃ | H | H | Cl(Br) |
| 2-i-C₃H₇ | H | H | i-C₃H₇ | H | H | CH₃ | Cl(Br) |
| 2-i-C₃H₇ | H | H | i-C₃H₇ | CH₃ | Cl | CH₃ | Cl(Br) |
| 2-i-C₃H₇ | H | H | i-C₃H₇ | H | OCH₃ | H | Cl(Br) |
| 2-sec.-C₄H₉ | H | H | i-C₃H₇ | H | H | H | Cl(Br) |
| 2-sec.-C₄H₉ | H | H | i-C₃H₇ | H | Cl | H | Cl(Br) |
| 2-sec.-C₄H₉ | H | H | i-C₃H₇ | CH₃ | H | CH₃ | Cl(Br) |
| 2-sec.-C₄H₉ | H | H | i-C₃H₇ | CH₃ | H | H | Cl(Br) |
| 2-sec.-C₄H₉ | H | H | i-C₃H₇ | H | H | CH₃ | Cl(Br) |
| 2-sec.-C₄H₉ | H | H | i-C₃H₇ | CH₃ | Cl | CH₃ | Cl(Br) |
| 2-sec.-C₄H₉ | H | H | i-C₃H₇ | H | OCH₃ | H | Cl(Br) |
| 2-tert.-C₄H₉ | H | H | i-C₃H₇ | H | H | H | Cl(Br) |
| 2-tert.-C₄H₉ | H | H | i-C₃H₇ | H | Cl | H | Cl(Br) |
| 2-tert.-C₄H₉ | H | H | i-C₃H₇ | CH₃ | H | CH₃ | Cl(Br) |
| 2-tert.-C₄H₉ | H | H | i-C₃H₇ | H | H | Cl(Br) | |
| 2-tert.-C₄H₉ | H | H | i-C₃H₇ | H | H | CH₃ | Cl(Br) |
| 2-tert.-C₄H₉ | H | H | i-C₃H₇ | CH₃ | Cl | CH₃ | Cl(Br) |
| 2-tert.-C₄H₉ | H | H | i-C₃H₇ | H | OCH₃ | H | Cl(Br) |
| 2-CH₃ | 6-CH₃ | H | i-C₃H₇ | H | H | H | Cl(Br) |
| 2-CH₃ | 6-CH₃ | H | i-C₃H₇ | H | Cl | H | Cl(Br) |
| 2-CH₃ | 6-CH₃ | H | i-C₃H₇ | CH₃ | H | CH₃ | Cl(Br) |
| 2-CH₃ | 6-CH₃ | H | i-C₃H₇ | CH₃ | H | H | Cl(Br) |
| 2-CH₃ | 6-CH₃ | H | i-C₃H₇ | H | H | CH₃ | Cl(Br) |
| 2-CH₃ | 6-CH₃ | H | i-C₃H₇ | CH₃ | Cl | CH₃ | Cl(Br) |
| 2-CH₃ | 6-CH₃ | H | i-C₃H₇ | H | OCH₃ | H | Cl(Br) |
| 2-CH₂H₅ | 6-CH₃ | H | i-C₃H₇ | H | H | Cl(Br) | |
| 2-C₂H₅ | 6-CH₃ | H | i-C₃H₇ | H | Cl | H | Cl(Br) |
| 2-C₂H₅ | 6-CH₃ | H | i-C₃H₇ | CH₃ | H | CH₃ | Cl(Br) |
| 2-C₂H₅ | 6-CH₃ | H | i-C₃H₇ | CH₃ | H | H | Cl(Br) |
| 2-C₂H₅ | 6-CH₃ | H | i-C₃H₇ | H | H | CH₃ | Cl(Br) |
| 2-C₂H₅ | 6-CH₃ | H | i-C₃H₇ | CH₃ | Cl | CH₃ | Cl(Br) |
| 2-C₂H₅ | 6-CH₃ | H | i-C₃H₇ | H | OCH₃ | H | Cl(Br) |
| 2-C₂H₅ | 6-C₂H₅ | H | i-C₃H₇ | H | H | H | Cl(Br) |
| 2-C₂H₅ | 6-C₂H₅ | H | i-C₃H₇ | H | Cl | H | Cl(Br) |
| 2-C₂H₅ | 6-C₂H₅ | H | i-C₃H₇ | CH₃ | H | CH₃ | Cl(Br) |
| 2-C₂H₅ | 6-C₂H₅ | H | i-C₃H₇ | CH₃ | H | H | Cl(Br) |
| 2-C₂H₅ | 6-C₂H₅ | H | i-C₃H₇ | H | H | CH₃ | Cl(Br) |
| 2-C₂H₅ | 6-C₂H₅ | H | i-C₃H₇ | CH₃ | Cl | CH₃ | Cl(Br) |
| 2-C₂H₅ | 6-C₂H₅ | H | i-C₃H₇ | H | OCH₃ | H | Cl(Br) |
| 2-CH₃ | 3-CH₃ | H | i-C₃H₇ | H | H | H | Cl(Br) |
| 2-CH₃ | 3-CH₃ | H | i-C₃H₇ | H | Cl | H | Cl(Br) |
| 2-CH₃ | 3-CH₃ | H | i-C₃H₇ | CH₃ | H | CH₃ | Cl(Br) |
| 2-CH₃ | 3-CH₃ | H | i-C₃H₇ | CH₃ | H | H | Cl(Br) |
| 2-CH₃ | 3-CH₃ | H | i-C₃H₇ | H | H | CH₃ | Cl(Br) |
| 2-CH₃ | 3-CH₃ | H | i-C₃H₇ | CH₃ | Cl | CH₃ | Cl(Br) |
| 2-CH₃ | 3-CH₃ | H | i-C₃H₇ | H | OCH₃ | H | Cl(Br) |
| 2-CH₃ | 3-CH₃ | 4-CH₃ | i-C₃H₇ | H | H | H | Cl(Br) |
| 2-CH₃ | 3-CH₃ | 4-CH₃ | i-C₃H₇ | H | Cl | H | Cl(Br) |
| 2-CH₃ | 3-CH₃ | 4-CH₃ | i-C₃H₇ | CH₃ | H | CH₃ | Cl(Br) |
| 2-CH₃ | 3-CH₃ | 4-CH₃ | i-C₃H₇ | CH₃ | H | H | Cl(Br) |
| 2-CH₃ | 3-CH₃ | 4-CH₃ | i-C₃H₇ | H | H | CH₃ | Cl(Br) |
| 2-CH₃ | 3-CH₃ | 4-CH₃ | i-C₃H₇ | CH₃ | Cl | CH₃ | Cl(Br) |
| 2-CH₃ | 3-CH₃ | 4-CH₃ | i-C₃H₇ | H | OCH₃ | H | Cl(Br) |
| 2-CH₃ | 5-CH₃ | H | i-C₃H₇ | H | H | H | Cl(Br) |
| 2-CH₃ | 5-CH₃ | H | i-C₃H₇ | H | Cl | H | Cl(Br) |
| 2-CH₃ | 5-CH₃ | H | i-C₃H₇ | CH₃ | H | CH₃ | Cl(Br) |

TABLE 1-continued

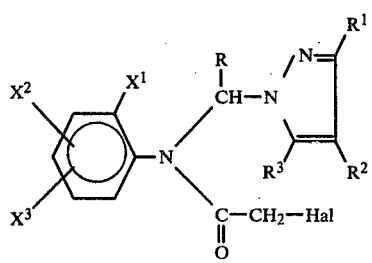
(I)

| X¹ | X² | X³ | R | R¹ | R² | R³ | Hal |
|---|---|---|---|---|---|---|---|
| 2-CH₃ | 5-CH₃ | H | i-C₃H₇ | CH₃ | H | H | Cl(Br) |
| 2-CH₃ | 5-CH₃ | H | i-C₃H₇ | H | H | CH₃ | Cl(Br) |
| 2-CH₃ | 5-CH₃ | H | i-C₃H₇ | CH₃ | Cl | CH₃ | Cl(Br) |
| 2-CH₃ | 5-CH₃ | H | i-C₃H₇ | H | OCH₃ | H | Cl(Br) |
| 2-CH₃ | H | H | C₂H₅ | H | H | H | Cl(Br) |
| 2-CH₃ | 6-CH₃ | H | C₂H₅ | H | H | H | Cl(Br) |
| 2-CH₃ | 6-C₂H₅ | H | C₂H₅ | H | H | H | Cl(Br) |
| 2-C₂H₅ | 6-C₂H₅ | H | C₂H₅ | H | H | H | Cl(Br) |
| 2-CH₃ | H | H | C₂H₅ | H | Cl | H | Cl(Br) |
| 2-CH₃ | 6-CH₃ | H | C₂H₅ | H | Cl | H | Cl(Br) |
| 2-CH₃ | 6-C₂H₅ | H | C₂H₅ | H | Cl | H | Cl(Br) |
| 2-C₂H₅ | 6-C₂H₅ | H | C₂H₅ | H | Cl | H | Cl(Br) |
| 2-CH₃ | H | H | C₂H₅ | CH₃ | H | CH₃ | Cl(Br) |
| 2-CH₃ | 6-CH₃ | H | C₂H₅ | CH₃ | H | CH₃ | Cl(Br) |
| 2-CH₃ | 6-C₂H₅ | H | C₂H₅ | CH₃ | H | CH₃ | Cl(Br) |
| 2-C₂H₅ | 6-C₂H₅ | H | C₂H₅ | CH₃ | H | CH₃ | Cl(Br) |
| 2-CH₃ | H | H | C₂H₅ | CH₃ | Cl | CH₃ | Cl(Br) |
| 2-CH₃ | 6-CH₃ | H | C₂H₅ | CH₃ | Cl | CH₃ | Cl(Br) |
| 2-CH₃ | 6-C₂H₅ | H | C₂H₅ | CH₃ | Cl | CH₃ | Cl(Br) |
| 2-C₂H₅ | 6-C₂H₅ | H | C₂H₅ | CH₃ | Cl | CH₃ | Cl(Br) |
| 2-CH₃ | H | H | n-C₃H₇ | H | H | H | Cl(Br) |
| 2-CH₃ | 6-CH₃ | H | n-C₃H₇ | H | H | H | Cl(Br) |
| 2-CH₃ | 6-C₂H₅ | H | n-C₃H₇ | H | H | H | Cl(Br) |
| 2-C₂H₅ | 6-C₂H₅ | H | n-C₃H₇ | H | H | H | Cl(Br) |
| 2-CH₃ | H | H | n-C₃H₇ | H | Cl | H | Cl(Br) |
| 2-CH₃ | 6-CH₃ | H | n-C₃H₇ | H | Cl | H | Cl(Br) |
| 2-CH₃ | 6-C₂H₅ | H | n-C₃H₇ | H | Cl | H | Cl(Br) |
| 2-C₂H₅ | 6-C₂H₅ | H | n-C₃H₇ | H | Cl | H | Cl(Br) |
| 2-CH₃ | H | H | n-C₃H₇ | CH₃ | H | CH₃ | Cl(Br) |
| 2-CH₃ | 6-CH₃ | H | n-C₃H₇ | CH₃ | H | CH₃ | Cl(Br) |
| 2-CH₃ | 6-C₂H₅ | n-C₃H₇ | CH₃ | H | CH₃ | Cl(Br) | |
| 2-C₂H₅ | 6-C₂H₅ | H | n-C₃H₇ | CH₃ | H | CH₃ | Cl(Br) |
| 2-CH₃ | H | H | n-C₃H₇ | CH₃ | Cl | CH₃ | Cl(Br) |
| 2-CH₃ | 6-CH₃ | H | n-C₃H₇ | CH₃ | Cl | CH₃ | Cl(Br) |
| 2-CH₃ | 6-C₂H₅ | H | n-C₃H₇ | CH₃ | Cl | CH₃ | Cl(Br) |
| 2-C₂H₅ | 6-C₂H₅ | H | n-C₃H₇ | CH₃ | Cl | CH₃ | Cl(Br) |

If, for example, 2-ethyl-6-methyl-chloroacetanilide and N-(1-chloroethyl)-pyrazole hydrochloride are used as the starting materials, the course of the reaction of the process according to the invention can be represented by the equation which follows:

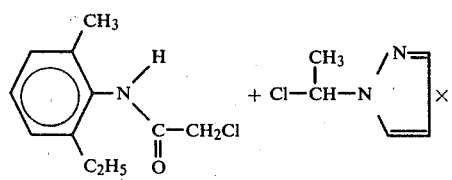
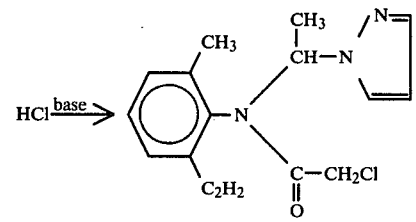

The formula (II) provides a general definition of the halogenoacetanilides required as starting substances in carrying out the process according to the invention. In this formula, Hal, $X^1$, $X^2$ and $X^3$ preferably have the meanings which have already been mentioned as preferred in connection with the compounds of the formula (I).

The haloacetanilides of the formula (II) are generally known, or they can be obtained in a manner which is generally known, by reacting corresponding anilines with a halogenoacetyl halide or halogenoacetic anhydride in the presence of an inert organic solvent, for example toluene or dimethylformamide, if appropriate in the presence of an acid-binding agent, for example potassium carbonate, at temperatures between 20° and 100° C. (see also the preparative examples later in this text).

Examples of haloacetanilides which may be mentioned are: chloro(bromo)acetanilide; 2-methyl-chloro(-bromo)acetanilide, 2-ethyl-chloro(bromo)acetanilide; 2-isopropyl-chloro(bromo)acetanilide; 2-sec.-butyl-chloro(bromo)acetanilide; 2-tert.-butyl-chloro(-bromo)acetanilide; 2,6-dimethyl-chloro(bromo)acetanilide; 2,3-dimethyl-chloro(bromo)acetanilide; 2,5-dimethyl-chloro(bromo)acetanilide; 3,5-dimethyl-chloro(bromo)acetanilide; 2,6-diethyl-chloro(-bromo)acetanilide; 2-ethyl-6-methyl-chloro(-bromo)acetanilide; 2,3,4-trimethyl-chloro(-bromo)acetanilide; 2,4,6-trimethyl-chloro(-bromo)acetanilide; 2,4,5-trimethyl-chloro(-bromo)acetanilide; 2-ethyl-4,6-dimethyl-chloro(-bromo)acetanilide; 2,6-diethyl-4-methyl-chloro(-bromo)acetanilide; 2,6-diisopropyl-4-methyl-chloro(-bromo)acetanilide and 2,3,5-trimethyl-chloro(-bromo)acetanilide.

The formula (III) provides a general definition of the pyrazolyl derivatives also to be used as starting materials for the reaction according to the invention. In this formula, R, R$^1$, R$^2$ and R$^3$ preferably have the meanings which have already been mentioned as preferred in connection with the compounds of the formula (I). Y preferably represents chlorine, bromine or the mesylate or tosylate radical.

The pyrazolyl derivatives of the formula (III) have not yet been described in the literature. They are obtained when known pyrazoles of the general formula

(IV)

in which R$^1$, R$^2$ and R$^3$ have the meanings stated above, are reacted with known aldehydes of the general formula

O=CH—R (V), in which R has the meaning stated above, if appropriate in the presence of an inert organic solvent, for example methylene chloride, at temperatures between −70° and +50° C., preferably at −20° to +30° C., and the new compounds thereby formed, of the general formula

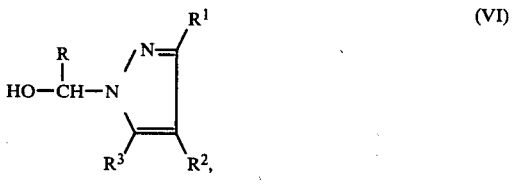

(VI)

in which R, R$^1$, R$^2$ and R$^3$ have the meanings stated above, are reacted directly, or if appropriate after being isolated, with a halogenating agent, such as, for example, thionyl chloride or phosphorus tribromide, or with a sulphonylating agent, such as mesyl chloride or tosyl chloride, if appropriate in the presence of an inert organic solvent, for example methylene chloride, at temperatures between −70° C. and +50° C., preferably at −20° C. to +30° C. The pyrazolyl derivatives of the formula (III) are thereby obtained in the form of hydrogen halide salts, depending on the halogenating agent or sulphonylating agent used. The pyrazolyl derivatives can then be liberated in the customary manner, but they can also be further reacted directly in the form of the hydrogen halide salts in which they are obtained (see also the preparative examples).

The compounds of the formula (VI) are in chemical equilibrium with their starting substances and can thus be isolated only in special cases.

Examples which may be mentioned of the pyrazolyl derivatives of the formula (III) are: 1-(1'-bromo(-chloro)ethyl)-pyrazole, 1-(1'-bromo(chloro)ethyl-4-chloropyrazole, 1-(1'-bromo(chloro)ethyl-2-methyl-pyrazole, 1-(1'-bromo(chloro)ethyl)-5-methyl-pyrazole, 1-(1'-bromo(chloro)ethyl)-3,5-dimethyl-pyrazole, 1-(1'-bromo(chloro)ethyl)-4-chloro-3,5-dimethyl-pyrazole, 1-(1'-bromo(chloro)ethyl)-4-methoxy-pyrazole, 1-(1'-bromo(chloro)propyl)-pyrazole, 1-(1'-bromo(chloro)-propyl)-4-chloro-pyrazole, 1-(1'-bromo(chloro)propyl)-3-methyl-pyrazole, 1-(1'-bromo(chloro)propyl)-5-methyl-pyrazole, 1-(1'-bromo(chloro)propyl)-3,5-dimethyl-pyrazole, 1-(1'-bromo(chloro)propyl)-4-chloro-3,5-dimethyl-pyrazole, 1-(1'-bromo(chloro)propyl)-4-methoxy-pyrazole, 1-(1'-bromo(chloro)butyl)-pyrazole, 1-(1'-bromo(chloro)butyl)-4-chloropyrazole, 1-(1'-bromo(chloro)butyl)-2-methyl-pyrazole, 1-(1'-bromo(-chloro)butyl)-5-methyl-pyrazole, 1-(1'-bromo(chloro)-butyl)-3,5-dimethyl-pyrazole, 1-(1'-bromo(chloro)-butyl)-4-chloro-3,5-dimethyl-pyrazole, 1-(1'-bromo(-chloro)butyl-4-methoxy-pyrazole, 1-(1'-bromo(chloro)-2'-methylpropyl)-pyrazole, 1(1'-bromo(chloro)-2'-methylpropyl)-4-chloro-pyrazole, 1-(1'-bromo(chloro)-2'-methylpropyl)-3-methyl-pyrazole, 1-(1'-bromo(-chloro)-2'-methylpropyl)-5-methyl-pyrazole, 1-(1'-bromo(chloro)-2'-methylpropyl)-3,5-dimethyl-pyrazole, 1-(1'-bromo(chloro)-2'-methyl-propyl)-4-chloro-3,5-dimethyl-pyrazole, 1-(1'-bromo(chloro)-2'-methyl-propyl)-4-methoxy-pyrazole, 1-(1'-bromo(-chloro)pentyl)-pyrazole, 1-(1'-bromo(chloro)pentyl)-4-chloro-pyrazole, 1-(1'-bromo(chloro)pentyl)-3-methyl-pyrazole, 1-(1'-bromo(chloro)pentyl)-5-methyl-pyrazole, 1-(1'-bromo(chloro)pentyl)-3,5-dimethyl-pyrazole, 1-(1'-bromo(chloro)pentyl)-4-chloro-3,5-dimethylpyrazole and 1-(1'-bromo(chloro)pentyl)-4-methoxy-pyrazole.

Any of the acids which lead to physiologically acceptable salts can be used for the preparation of acid addition salts of the compounds of the formula (I). These acids include, as preferences, the hydrogen halide acids (for example hydrobromic acid and, in particular, hydrochloric acid), phosphoric acid, nitric acid, sulphuric acid, monofunctional and bifunctional carboxylic acids and hydroxycarboxylic acids (for example acetic acid, maleic acid, succinic acid, fumaric acid, tartaric acid, citric acid, salicylic acid, sorbic acid, and lactic acid), and sulphonic acids (for example p-toluenesulphonic acid and 1,5-naphthalenedisulphonic acid).

The salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtration and if appropriate purified by washing with an inert organic solvent.

Salts of metals of main groups II to IV and of sub-groups I and II and IV to VIII are preferably used for the preparation of metal salt complexes of the compounds of the formula (I), examples of such metals being copper, zinc, manganese, magnesium, tin, iron and nickel. Possible anions of the salts are those which are derived from acids, which lead to physiologically acceptable salts, preferably the hydrogen halide acids (for example hydrochloric acid and hydrobromic acid), phosphoric acid, nitric acid and sulphuric acid.

The metal salt complexes of the compounds of the formula (I) can be obtained in a simple manner by customary processes, for example, by dissolving the metal salt in alcohol, for example ethanol, and adding the solution to the compound of the formula (I). The metal salt complexes can then be isolated in a known manner, for example by filtration, and if appropriate purified by recrystallization.

Possible solvents for the reaction according to the invention are any of the inert, water-immiscible, organic solvents. These include, as preferences, ethers, such as diethyl ether; aromatic hydrocarbons, such as benzene, toluene or xylene; halogenated hydrocarbons, such as methylene chloride, carbon tetrachloride, chloroform or chlorobenzene; and esters such as ethyl acetate.

The reaction according to the invention is carried out in the presence of an acid-binding agent. Any of the customary acid-binding agents can be used in this case, especially inorganic bases, for example alkali metal hydroxides and alkali metal carbonates.

The reaction temperatures can be caried within a substantial range in carrying out the process according to the invention. In general, the process is carried out at from $-70°$ C. to $+100°$ C., preferably at from $-20°$ C. to $+80°$ C.

In carrying out the process according to the invention, 0.5 to 2.0 moles of pyrazole derivative of the formula (III) and 1 to 10 moles of acid-binding agent are preferably employed per mole of haloacetanilides of the formula (II). Isolation of the compounds of the formula (I) is effected in the customary manner.

In a preferred embodiment, the reaction according to the invention is carried out in a two-phase system, for example aqueous sodium hydroxide solution or potassium hydroxide solution/toluene or methylene chloride, if appropriate with the addition of 0.01–1 mole of a phase transfer catalyst, for instance an ammonium or phosphonium compound, benzyl-dodecyl-dimethyl-ammonium chloride (Zephirol) being mentioned as an example.

According to one variant of the process according to the invention, it is possible to react anilines of the formula

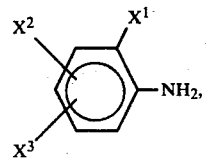

in which $X^1$, $X^2$ and $X^3$ have the meaning stated above, in a manner corresponding to the procedure of the above-described process according to the invention, first with pyrazole derivatives of the formula (III), it also being possible to use an excess of aniline of the formula (VII) as an acid-binding agent, and then to react the substituted secondary anilines thus obtained of the general formula

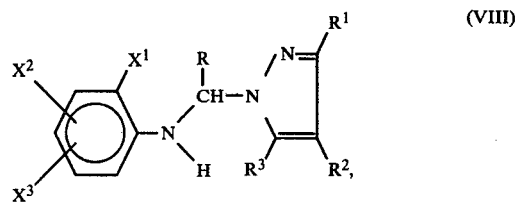

in which R, $R^1$, $R^2$, $R^3$, $X^1$, $X^2$ and $X^3$ have the meaning stated above, with a halogenoacetyl halide or halogenoacetic anhydride in the presence of an inert organic solvent, for example toluene or dimethylformamide, if appropriate in the presence of an acid-binding agent, for example potassium carbonate, at temperatures of from $20°$ C. to $100°$ C.

The active compounds according to the invention influence plant growth and can therefore be used as defoliants, desiccants, agents for destroying broad-leaved plants, germination inhibitors and, especially, as weed-killers. By "weeds" in the broadest sense there are meant plants growing in places where they are not desired. Whether the compounds according to the invention act as total herbicides or selective herbicides depends essentially on the amount used.

The active compounds according to the present invention may be used, for example, to combat the following plants:

dicotyledon weeds of the genera Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea, and monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

The active compounds according to the present invention may be used, for example, as selective herbicides in the following cultures:

dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita, and monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

Depending on the concentration, the compounds can be used for the total combating of weeds, for example on industrial terrain and railway tracks and on paths and squares with and without trees. Equally, the compounds can be employed for combating weeds in perennial cultures, for example forestry plantings, decorative tree plantings, orchards, vineyards, citrus groves, nut orchards, banana plantations, coffee plantations, tea plantations, rubber plantations, oil palm plantations, cacao plantations, soft fruit plantings and hopfields, and for the selective combating of weeds in annual cultures.

In addition to a very good action against graminaceous weeds, the active compounds according to the invention in particular also exhibit a good herbicidal action in the case of broad-leaved weeds. It is possible to use the active compounds according to the invention for selectively combating weeds, preferably in maize, groundnut, beet, soya bean, cotton, rice and varieties of cereal.

The active compounds can be converted into the customary formulations, such as solutions, emulsions, wettable powders, suspensions, powders, dusting agents, pastes, soluble powders, granules, suspension-emulsion concentrates, natural and synthetic materials impregnated with active compound and very fine capsules in polymeric substances.

These formulations may be produced in known manner, for example by mixing the active compounds with extenders, that is to say liquid or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention, either as such or in their formulations, can also be used, for the combating of weeds, in admixture with known herbicides, finished formulations or tank mixing being possible.

The active compounds according to the invention can be present in the formulations, or in the various use forms, as a mixture with other active compounds, such as fungicides, insecticides, acaricides, nematicides, herbicides, bird repellants, growth factors, plant nutrients and agents for improving soil structure.

The active compounds can be used as such, as their formulations or as the use forms prepared therefrom by further dilution, such as ready-to-use solutions, emulsions, suspensions, powders, pastes and granules. They are used in the customary manner, for example by watering, spraying, atomizing and scattering.

The active compounds according to the invention can be applied either before or after emergence of the plants. They are preferably applied before emergence of the plants, that is to say by the pre-emergence process. They can also be incorporated into the soil before sowing.

The amount of active compound used can vary within a substantial range. It depends essentially on the nature of the desired effect. In general, the amounts used are from 0.1 to 10 kg of active compound per ha, preferably from 0.1 to 5 kg/ha.

When used by the post-emergence process, the active compounds according to the invention also exhibit growth regulating properties and are suitable as growth regulators.

The present invention also provides a herbicidal composition containing as active ingredient a compound of the present invention in admixture with a solid or liquefied gaseous diluent or carrier or in admixture with a liquid diluent or carrier containing a surface-active agent.

The present invention also provides a method of combating weeds which comprises applying to the weeds, or to a habitat thereof, a compound of the present invention alone or in the form of a composition containing as active ingredient a compound of the present invention in admixture with a diluent or carrier.

The present invention further provides crops protected from damage by weeds by being grown in areas in which immediately prior to and/or during the time of the growing a compound of the present invention was applied alone or in admixture with a diluent or carrier.

It will be seen that the usual methods of providing a harvested crop may be improved by the present invention.

The selective herbicidal activity of the compounds of this invention is illustrated by the following biotest Example.

In this Example, the compounds according to the present invention are each identified by the number (given in brackets) of the corresponding preparative Example, which will be found later in this specification.

The known comparison compound is identified as follows:

(A) = 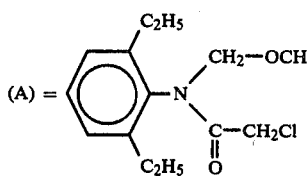

(2,6-diethyl)-N-methoxymethyl-chloroacetanilide.

EXAMPLE A

Pre-emergence test

Solvent: 5 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

Seeds of the test plants were sown in normal soil and, after 24 hours, watered with the preparation of the active compound. It was expedient to keep constant the amount of water per unit area. The concentration of the active compound in the preparation was of no importance, only the amount of active compound applied per unit area being decisive. After three weeks, the degree of damage to the plants was determined in % damage in comparison to the development of the untreated control. The figures denoted:

0%=no action (like untreated control)
100%=total destruction

In this test, the active compounds (2) and (3) exhibited a better selective activity than the substance (A) known from the prior art.

PREPARATIVE EXAMPLES

Example 1

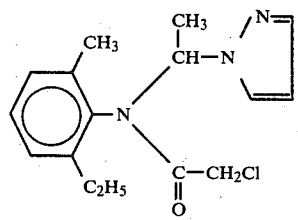 (1)

42.3 g (0.2 mol) of 2-ethyl-6-methyl-chloroacetanilide and 36.8 g (0.22 mol) of N-(1-chloroethyl)-pyrazole hydrochloride were dissolved in 200 ml of methylene chloride. After adding 0.5 ml of Zephirol (50% strength aqueous solution of benzyl-dodecyl-dimethylammonium chloride) a solution of 80 g (2 mol) of sodium hydroxide in 80 ml of water was added dropwise, while stirring vigorously, whereupon the reaction mixture heated up to the reflux temperature. The reaction mixture was stirred for about a further 3 hours until it had cooled to room temperature. The organic phase was separated off, washed several times with water until neutral, dried over sodium sulphate and concentrated in vacuo. A colorless oil was obtained as the residue and crystallized completely after some time. Yield: 29 g (47.5% of theory) of 2-ethyl-6-methyl-N-(pyrazol-1-yl-eth-1-yl)-chloroacetanilide in the form of white crystals of melting point 74° C. The substance could be purified by recrystallizing several times from diethyl ether, and then had a melting point of 84° C.

PREPARATION OF THE PRECURSORS

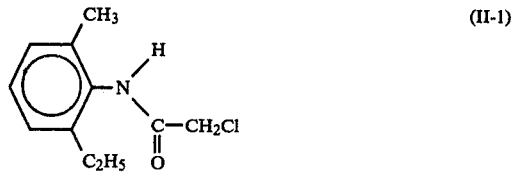 (II-1)

152 g (1.1 mol) of potassium carbonate were added to 135.2 g (1 mol) of 2-ethyl-6-methyl-aniline in 1,000 ml of toluene. 113 g (1 mol) of chloroacetyl chloride were added dropwise to this mixture, while stirring. When the exothermic reaction had subsided, the mixture was subsequently stirred under reflux for 2 hours. The reaction mixture was then filtered and the filtrate was concentrated to 500 ml in vacuo. The crystals thereby formed were filtered off and washed with petroleum ether. 202.9 g (96.2% of theory) of 2-ethyl-6-methyl-chloroacetanilide were obtained in the form of white crystals of melting point 120° C.

 (III-1)

250 g (5.7 mol) of acetaldehyde were added dropwise to 340 g (5 mol) of pyrazole in 1200 ml of methylene chloride at 0° to 5° C. in the course of 1 hour. The mixture was subsequently stirred at 0° C. for about 1 hour. The N-(1-hydroxyethyl)-pyrazole (VI-1) thereby formed was not isolated, but the reaction solution was directly added dropwise to 1250 g (10.5 mol) of thionyl chloride at 0° to 5° C. and in the course of one hour. The mixture was subsequently stirred at 20° C. for 1 hour and then concentrated at 40° C. in vacuo. After adding 300 ml of methylene chloride to the residue, the mixture was again concentrated. The residue was distilled in vacuo. 620.3 g (75% of theory) of N-(1-chloroethyl)-pyrazole hydrochloride of boiling point 55° C./18 mm Hg were obtained.

Those compounds listed in Table 2 below were obtained in a corresponding manner.

TABLE 2

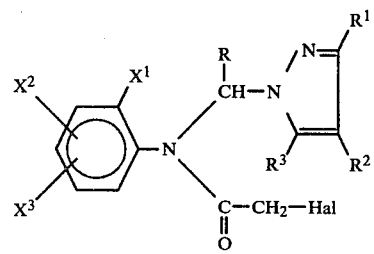 (I)

| Example No. | $X^1$ | $X^2$ | $X^3$ | R | $R^1$ | $R^2$ | $R^3$ | Hal | Melting point (°C.) |
|---|---|---|---|---|---|---|---|---|---|
| 2 | $CH_3$ | 6-$CH_3$ | H | $CH_3$ | H | H | H | Cl | 90 |
| 3 | $C_2H_5$ | 6-$C_2H_5$ | H | $CH_3$ | H | H | H | Cl | 80 |
| 4 | $CH_3$ | 6-$C_2H_5$ | H | $CH_3$ | H | H | H | Cl | 95 (× HCl) |

The starting materials of the formula (II) listed in Table 3 below were obtained by the known process.

TABLE 3

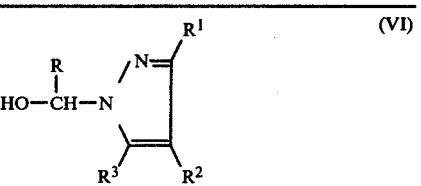

(II)

| Example No. | $X^1$ | $X^2$ | $X^3$ | Hal | Melting point (°C.) |
|---|---|---|---|---|---|
| II-2 | $CH_3$ | 6-$CH_3$ | H | Cl | 148 |
| II-3 | $C_2H_5$ | 6-$C_2H_5$ | H | Cl | 133 |
| II-4 | i-$C_3H_7$ | H | H | Cl | 79 |
| II-5 | tert.-$C_4H_9$ | H | H | Cl | 96 |
| II-6 | $C_2H_5$ | H | H | Cl | 103 |
| II-7 | $CH_3$ | H | H | Cl | 109 |
| II-8 | $CH_3$ | 3-$CH_3$ | H | Cl | 135 |
| II-9 | $CH_3$ | 5-$CH_3$ | H | Cl | 154 |
| II-10 | $CH_3$ | 4-$CH_3$ | 6-$CH_3$ | Cl | 177 |
| II-11 | $C_2H_5$ | 4-$CH_3$ | 6-$CH_3$ | Cl | 134 |
| II-12 | sec.-$C_4H_9$ | H | H | Cl | oil |
| II-13 | H | H | H | Cl | 132 |

The starting materials of the formula (III) listed in Table 4 below were obtained by the process described above in this specification.

TABLE 4

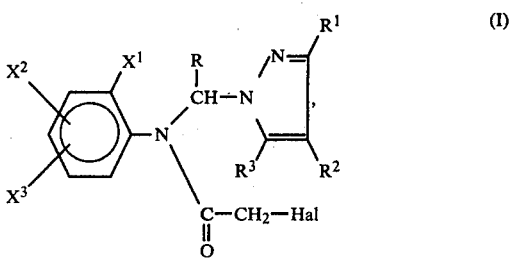

(III)

| Example No. | R | $R^1$ | $R^2$ | $R^3$ | Y | Physical constants |
|---|---|---|---|---|---|---|
| III 2 | —i-$C_3H_7$ | H | H | H | cl | Melting point: 114° C.(× HCl) |
| III 3 | —$CCl_3$ | H | H | H | Cl | Melting point: 95° C.(× HCl) |
| III 4 | —$CH_3$ | $CH_3$ | Cl | $CH_3$ | Cl | Oil (× HCl) |
| III 5 | —$CH_3$ | H | Cl | H | Cl | Boiling point: 60-62° C./20 mb (× HCl) |
| III 6 | —$C_2H_5$ | H | H | H | Cl | Oil (× HCl) |
| III 7 | —n-$C_3H_7$ | H | H | H | Cl | Oil (× HCl) |
| III 8 | —$CH_3$ | H | H | H | Br | Boiling point: 60-65° C./20 mb |
| III 9 | —$CH_3$ | H | H | H | Cl | Boiling point: 50-55° C./18 mb |

The intermediate products of the formula (VI) listed in Table 5 below were obtained by the process described in this specification.

TABLE 5

(VI)

$$\begin{array}{c} R^1 \\ R \quad /N= \\ HO-CH-N \\ \quad \backslash \\ R^3 \quad R^2 \end{array}$$

| Example No. | R | $R^1$ | $R^2$ | $R^3$ | Physical constants |
|---|---|---|---|---|---|
| VI-2 | i-$C_3H_7$ | H | H | H | not isolated |
| VI-3 | —$CCl_3$ | H | H | H | Melting point: 109° C. |
| VI-4 | —$CH_3$ | $CH_3$ | Cl | $CH_3$ | Melting point: 39–44° C. |

It will be understood that the specification and examples are illustrative, but not limitative of the present invention and that other embodiments within the spirit and scope of the invention will suggest themselves to those skilled in the art.

What is claimed is:

1. Substituted N-pyrazolylmethyl-haloacetanilide compound of the formula $$\begin{array}{c} R^1 \\ X^1 \quad R \quad /N= \\ X^2 \quad \quad CH-N \\ \quad \quad N \quad \backslash \\ X^3 \quad | \quad R^3 \quad R^2 \\ C-CH_2-Hal \\ \| \\ O \end{array}$$ (I)

wherein

Hal is halogen;

R is cycloalkyl of from 3 to 6 carbon atoms, haloalkyl with up to 2 carbon atoms and up to 3 halogen atoms, alkoxyalkyl of from 1 to 4 carbon atoms in the alkyl part and from 1 to 4 carbon atoms in alkoxy part, alkenyl or alkynyl of from 2 to 4 carbon atoms each or optionally substituted phenyl the substitutents being selected from halogen, alkyl with 1 to 4 carbon atoms, haloalkyl with up to 2 carbon atoms and up to 3 identical or different halogen atoms, alkoxy and alkylthio with in either case up to 2 carbon atoms, cyano and nitro;

$R^1$, $R^2$ and $R^3$ are individually selected from hydrogen, alkyl, halogen or alkoxy with from 1 to 4 carbon atoms each; and $X^1$, $X^2$ and $X^3$ are individually selected from hydrogen or alkyl with from 1 to 4 carbon atoms, and the hydrochloric acid addition salts of such compounds.

2. Substituted N-pyrazolylmethyl-haloacetanilide compound as claimed in claim 1 wherein Hal is fluorine, chlorine or bromine.

3. Substituted N-pyrazolylmethyl-haloacetanilide compound as claimed in claim 1 wherein R is cycloalkyl of 3 to 6 ring carbon atoms.

4. Substituted N-pyrazolylmethyl-haloacetanilide compound as claimed in claim 1 wherein R is haloalkyl of up to 2 carbon atoms and up to 3 halogen atoms.

5. Substituted N-pyrazolylmethyl-haloacetanilide compound as claimed in claim 1 wherein R is alkoxyalkyl of 1 to 4 carbon atoms in each alkyl moiety.

6. Substituted N-pyrazolylmethyl-haloacetanilide compound as claimed in claim 1 wherein R is alkenyl or alkynyl of up to 4 carbon atoms.

7. Substituted N-pyrazolylmethyl-haloacetanilide compound as claimed in claim 1 wherein R is phenyl.

8. Substituted N-pyrazolylmethyl-haloacetanilide compound as claimed in claim 1 wherein R is substituted phenyl wherein the substituent is at least one of the group selected from halogen, alkyl of up 4 carbon atoms, haloalkyl of up to 2 carbon atoms and up to 3 halogen atoms, alkoxy or alkylthio of up to 2 carbon atoms, cyano and nitro.

9. Substituted N-pyrazolylmethyl-haloacetanilide compound as claimed in claim 1 wherein $R^1$ is hydrogen.

10. Substituted N-pyrazolylmethyl-haloacetanilide compound as claimed in claim 1 wherein $R^2$ is hydrogen.

11. Substituted N-pyrazolylmethyl-haloacetanilide compound as claimed in claim 1 wherein $R^3$ is hydrogen.

12. Substituted N-pyrazolylmethyl-haloacetanilide compound as claimed in claim 1 wherein $R^1$ is alkyl of up to 4 carbon atoms.

13. Substituted N-pyrazolylmethyl-haloacetanilide compound as claimed in claim 1 wherein $R^2$ is alkyl of up to 4 carbon atoms.

14. Substituted N-pyrazolylmethyl-haloacetanilide compound as claimed in claim 1 wherein $R^3$ is alkyl of up to 4 carbon atoms.

15. Substituted N-pyrazolylmethyl-haloacetanilide compound as claimed in claim 1 wherein $R^1$ is halogen.

16. Substituted N-pyrazolylmethyl-haloacetanilide compound as claimed in claim 1 wherein $R^2$ is halogen.

17. Substituted N-pyrazolylmethyl-haloacetanilide compound as claimed in claim 1 wherein $R^3$ is halogen.

18. Substituted N-pyrazolylmethyl-haloacetanilide compound as claimed in claim 1 wherein $R^1$ is alkoxy of up to 4 carbon atoms.

19. Substituted N-pyrazolylmethyl-haloacetanilide compound as claimed in claim 1 wherein $R^2$ is alkoxy of up to 4 carbon atoms.

20. Substituted N-pyrazolylmethyl-haloacetanilide compound as claimed in claim 1 wherein $R^3$ is alkoxy of up to 4 carbon atoms.

21. Substituted N-pyrazolylmethyl-haloacetanilide compound as claimed in claim 1 wherein $X^1$ is hydrogen.

22. Substituted N-pyrazolylmethyl-haloacetanilide compound as claimed in claim 1 wherein $X^2$ is hydrogen.

23. Substituted N-pyrazolylmethyl-haloacetanilide compound as claimed in claim 1 wherein $X^3$ is hydrogen.

24. Substituted N-pyrazolylmethyl-haloacetanilide compound as claimed in claim 1 wherein $X^1$ is alkyl of up to 4 carbon atoms.

25. Substituted N-pyrazolylmethyl-haloacetanilide compound as claimed in claim 1 wherein $X^2$ is alkyl of up to 4 carbon atoms.

26. Substituted N-pyrazolylmethyl-haloacetanilide compound as claimed in claim 1 wherein $X^3$ is alkyl of up to 4 carbon atoms.

27. Substituted N-pyrazolylmethyl-haloacetanilide compound of the formula

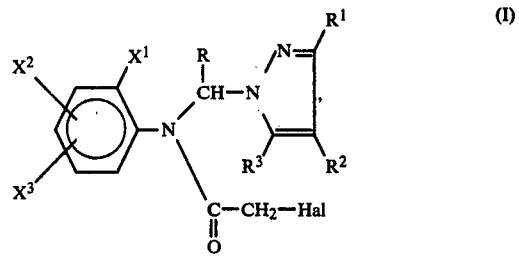

wherein
Hal is chlorine
R is phenyl optionally substituted by chlorine
$R^1$ is hydrogen or alkyl with 1 to 4 carbon atoms
$R^2$ is hydrogen, alkyl with 1 to 4 carbon atoms, halogen or alkoxy with 1 to 4 carbon atoms,
$R^3$ is hydrogen or alkyl with 1 to 4 carbon atoms,
$X^1$ is hydrogen or alkyl with 1 to 4 carbon atoms,
$X^2$ is hydrogen or alkyl with 1 to 4 carbon atoms, and
$X^3$ is hydrogen
and the hydrochloric acid addition salts thereof.

28. Substituted N-pyrazolylmethyl-haloacetanilide compounds as claimed in claim 1 wherein
Hal is chlorine or bromine,
R is trifluoromethyl, chloromethyl, dichloromethyl, trichloromethyl, tribromomethyl, vinyl, allyl, propen-1-yl, ethynyl, propargyl, phenyl, chlorophenyl, dichlorophenyl, methylphenyl, dimethylphenyl, chloromethylphenyl or nitrophenyl;
$R^1$, $R^2$ and $R^3$ are individually selected from hydrogen, methyl, chlorine, bromine or methoxy; and
$X^1$, $X^2$ and $X^3$ are individually selected from hydrogen, methyl, ethyl, n-propyl, isopropyl, isobutyl, sec.-butyl or tert.-butyl.

29. Substituted N-pyrazolylmethyl-haloacetanilide compound as claimed in claim 1 in the form of its acid addition salt.

30. A herbicidal composition comprising an agriculturally acceptable carrier and in effective amounts a substituted N-pyrazolylmethyl-haloacetanilide compound as claimed in claim 1.

31. Method of combating weeds which method comprises applying to an area of cultivation, an effective amount of a substituted N-pyrazolylmethyl-haloacetanilide compound as claimed in claim 1.

* * * * *